US012629274B2

(12) United States Patent
Sakamoto

(10) Patent No.: US 12,629,274 B2
(45) Date of Patent: May 19, 2026

(54) FINGER BRACE

(71) Applicant: Keizo Sakamoto, Kanagawa (JP)

(72) Inventor: Keizo Sakamoto, Kanagawa (JP)

( * ) Notice: Subject to any disclaimer, the term of this patent is extended or adjusted under 35 U.S.C. 154(b) by 0 days.

(21) Appl. No.: 18/847,445

(22) PCT Filed: Mar. 7, 2024

(86) PCT No.: PCT/JP2024/008844

§ 371 (c)(1),
(2) Date: Sep. 16, 2024

(87) PCT Pub. No.: WO2024/190619

PCT Pub. Date: Sep. 19, 2024

(65) Prior Publication Data

US 2025/0332016 A1 Oct. 30, 2025

(30) Foreign Application Priority Data

Mar. 10, 2023 (JP) ................................. 2023-037880

(51) Int. Cl.
*A61F 5/01* (2006.01)
*A61F 5/058* (2006.01)
*A61F 5/10* (2006.01)

(52) U.S. Cl.
CPC ........ *A61F 5/0118* (2013.01); *A61F 5/05875* (2013.01); *A61F 5/10* (2013.01)

(58) Field of Classification Search
CPC ........ A61F 5/01; A61F 5/0111; A61F 5/0118; A61F 5/013; A61F 5/05875; A61F 5/10; A61F 13/00059; A61F 13/02; A61F 13/0269; A61F 13/0273; A61F 13/10; A61F 13/104; A61F 13/105; A41D 13/08; A41D 13/081; A41D 13/087
USPC ................................... 602/21, 22, 30, 54, 55
See application file for complete search history.

(56) References Cited

U.S. PATENT DOCUMENTS

| | | | | | |
|---|---|---|---|---|---|
| 817,416 | A | * | 4/1906 | Cather | A41D 13/08 |
| | | | | | 2/59 |
| 2003/0055369 | A1 | * | 3/2003 | Siegwart | A61F 13/0203 |
| | | | | | 602/54 |
| 2010/0137769 | A1 | * | 6/2010 | Schulte | A61F 5/05875 |
| | | | | | 602/22 |

(Continued)

FOREIGN PATENT DOCUMENTS

| | | |
|---|---|---|
| JP | 2004-261398 A | 9/2004 |
| JP | 2018-050762 A | 4/2018 |

*Primary Examiner* — Alireza Nia
*Assistant Examiner* — Seth R. Brown
(74) *Attorney, Agent, or Firm* — Carrier, Shende & Associates P.C.; Joseph P. Carrier; Fulchand P. Shende

(57) ABSTRACT

A finger brace for use in the treatment of finger tendovaginitis includes a tape component formed in a band shape of prescribed length and width, an elastically deformable pad provided at a prescribed position along a longitudinal axis of the tape component, and an adhesive part provided on the tape component so as to join the two layers of the tape component to each other when the tape component is wrapped around a intended finger. Owing to a first guideline provided along the longitudinal axis of the tape component offset from the lateral midpoint of the tape component by a prescribed distance, the patient can wear the finger brace at the appropriate position on the affected part.

6 Claims, 7 Drawing Sheets

(56)     References Cited

U.S. PATENT DOCUMENTS

Figure 1:
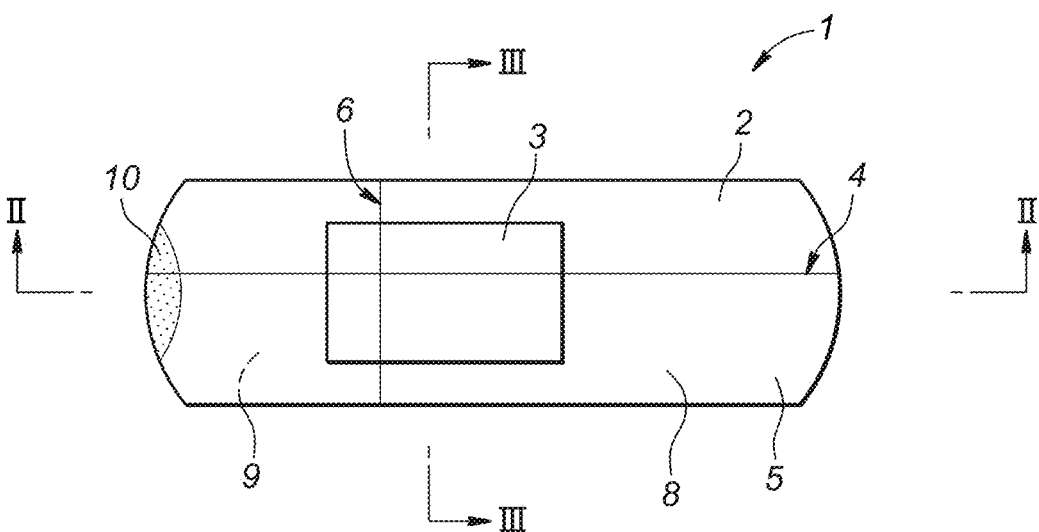

| | | | |
|---|---|---|---|
| 2016/0106595 A1* | 4/2016 | Arbesman | A61F 13/00085 |
| | | | 602/54 |
| 2018/0325742 A1* | 11/2018 | Millet | A61F 5/0106 |

* cited by examiner (A)

(B)

FINGER BRACE

TECHNICAL FIELD

The present invention relates to a finger brace used for the treatment of finger tendovaginitis.

BACKGROUND ART

When a finger develops tendovaginitis, the finger (proximal interphalangeal joint [PIP-J] portion) may become stiff and be kept bent at about 90 degrees under various circumstances such as while sleeping, for instance. In such cases, forcibly extending the finger may cause not only pain, but also the click of a "trigger finger". As a means of treating finger tendovaginitis, methods such as ointments, injections, and surgery are conventionally used.

However, ointments and injections do not provide a fundamental cure for finger tendovaginitis. Furthermore, although surgery is more effective than ointments and injections, many patients prefer to avoid surgery. For these reasons, fixation materials are known to fix the patient's finger to prevent bending (for example, see Patent Document 1). The fixation material disclosed in Patent Document 1 has a base made of a sheet or film and multiple reinforcing parts made of highly rigid materials fixed to the base at intervals.

PRIOR ART DOCUMENT(S)

Patent Document(s)

PATENT DOCUMENT 1: JP2004-261398A

SUMMARY OF THE INVENTION

Task to be Accomplished by the Invention

The fixation material disclosed in Patent Document 1 has a structure that covers parts of the finger other than the affected part. In addition, since reinforcing parts are intended to fix and hold the joint, and are excessive rigid, the affected finger is excessively fixed in an extended state. Here, the concept that the entire finger is "excessively fixed" means not only that the finger is completely fixed in the extended state, but also that the bending function of the finger is hindered. This can cause problems such as significant restriction to daily finger-bending movements such as grasping objects, and increases the risk of joint disorders developing due to excessive fixation of the finger.

Given the above background, the primary objective of the present invention is to provide a finger brace for use in the treatment of finger tendovaginitis, that can be easily worn by the patient and that can fix the affected finger sufficiently without excessive fixation. In this context, "softly fixing" the finger means fixing the finger to such an extent as to not interfere with the physiological function of the finger, i.e., to such an extent as to not adversely impair the finger-bending movements required in activities of daily living.

Means to Accomplish the Task

The finger brace (1) according to an embodiment of the present invention comprises
a tape component (2) formed in a band shape and having a prescribed length and width, an elastically deformable pad (3) provided at a prescribed position along a longitudinal axis of the tape component (2),
a first guideline (4) provided along the longitudinal axis of the tape component (2) and offset from a lateral midpoint of the tape component (2) by a prescribed distance, and
an adhesive part (5) provided on the tape component (2) so as to join two layers of the tape component (2) to each other when the tape component (2) is wrapped around a finger.

According to this configuration, first, the finger brace (1) is applied to a side of the affected area so as to be perpendicular to a longitudinal axis of the finger and offset the first guideline (4) toward the fingertip. Next, the first guideline (4) is aligned with a joint crease on the palmar side (PIP-J part) of the finger, the tape component (2) is wrapped around the finger under appropriate tension, and the tape component (2) is held wrapped around the finger using the adhesive part (5). Since the position of the finger joint is anatomically slightly offset from the joint crease on the palmar side, determining the position of the finger joint from the outside is difficult. However, since the first guideline (4) is provided at a position offset from the midpoint of the lateral axis of the tape component (2) by an appropriate distance, the tape component (2) can be wrapped around the position of the finger that correctly aligns with the finger joint by aligning the first guideline (4) with the joint crease on the palmar side. In addition, by imparting the pad (3) with suitable elasticity, the risk of excessively fixing the affected finger is removed.

In this finger brace (1), preferably, the first guideline (4) is a line extending along the longitudinal axis and passing through a point at which the tape component (2) is divided by a ratio of 3 to 2 along the lateral axis.

According to this configuration, when the patient wears the finger brace (1) on the affected finger, the pad (3) is easily adapted to the appropriate position of the finger that includes the PIP-J portion.

In this finger brace (1), preferably, the pad (3) is 1.5 to 3.5 cm long along a longitudinal axis thereof.

According to this configuration, the length of the pad (3) can be appropriately selected according to the thickness of the finger of the specific patient.

In this finger brace (1), preferably, a second guideline (6) extending along the lateral axis of the tape component (2) is provided on the pad (3) adjacent to a longitudinal edge thereof.

According to this configuration, the patient can accurately and easily align the pad (3) with the position on the palmar side of the finger corresponding to the joint by aligning the second guideline (6) with a profile of the palmar side of the finger as viewed from the side.

In this finger brace (1), preferably, the pad (3) is made of a material that is structured to be less readily stretchable along the lateral axis than along the longitudinal axis.

According to this configuration, the patient can appropriately suppress flexion and extension of the affected area while ensuring comfort.

In this finger brace (1), preferably, a midpoint of the pad (3) along the longitudinal axis is offset to one side along the longitudinal axis with respect to a midpoint of the tape component (2) along the longitudinal axis.

According to this configuration, when the patient is about to wear the finger brace (1), the pad (3) is easily visible so that positioning of the pad (3) on the palmar side of the finger is facilitated.

In this finger brace (1, 201), preferably, marks (7) indicating the wrapping thickness of the tape component (2) are provided at parts of the tape component (2) where the tape component overlaps with itself when wrapped around the finger.

According to this configuration, when the patient wears the finger brace (1), the wrapping thickness can be easily selected depending on the thickness of the patient's finger and the healing status of the affected area.

Effect of the Invention

According to this configuration, the patient can easily wear the finger brace (1) on the finger without excessively fixing affected finger.

BRIEF DESCRIPTION OF THE DRAWING(S)

Figure 2:
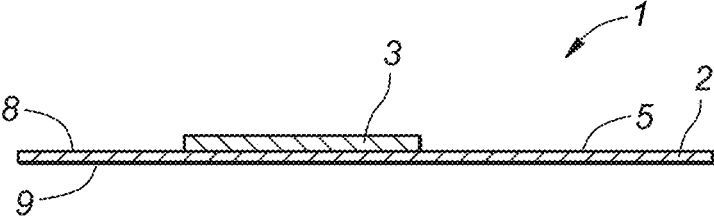

FIG. 1 a view showing the finger brace according to a first embodiment of the present invention FIG. 2 a sectional view taken along line II-II of FIG. 1

Figure 3:
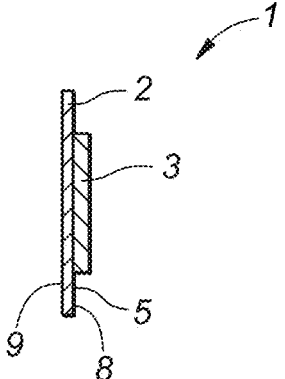

FIG. 3 a sectional view taken along line III-III of FIG. 1

Figure 4:
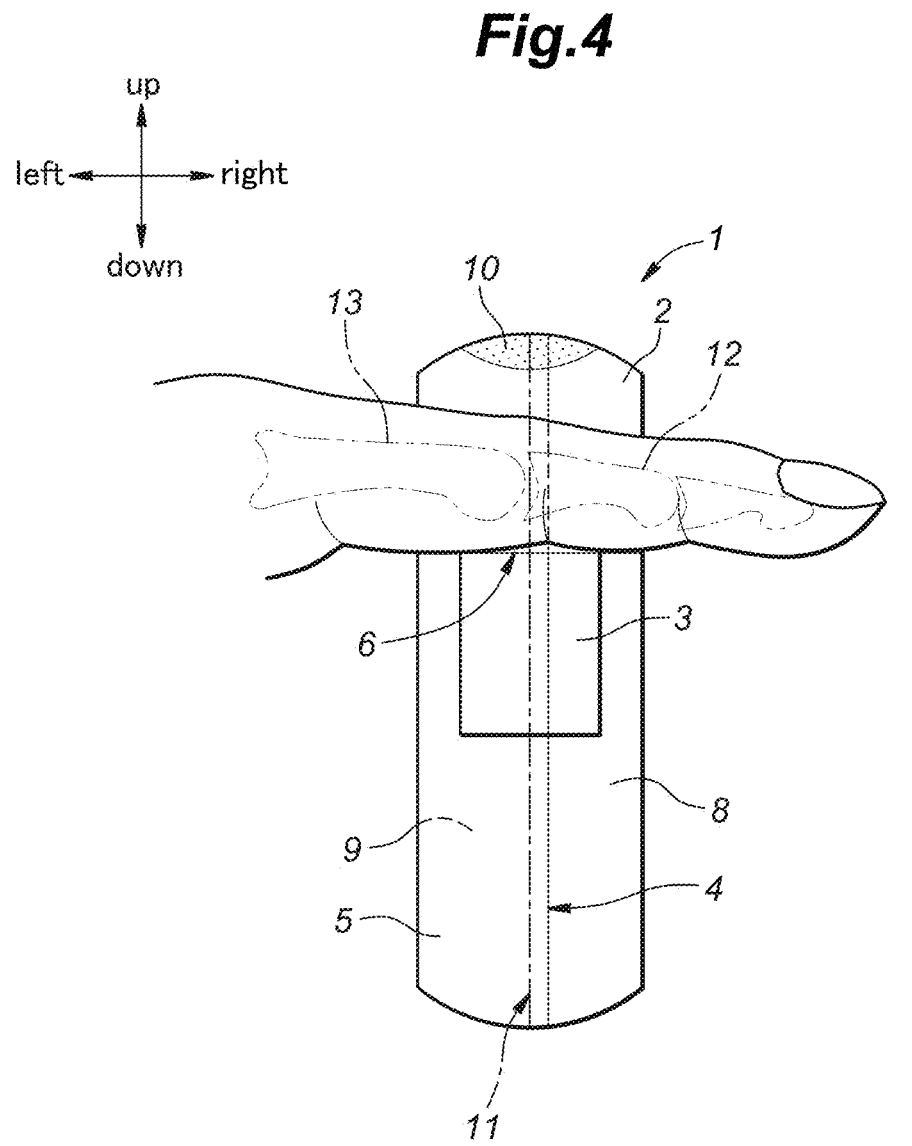
Figure 5:
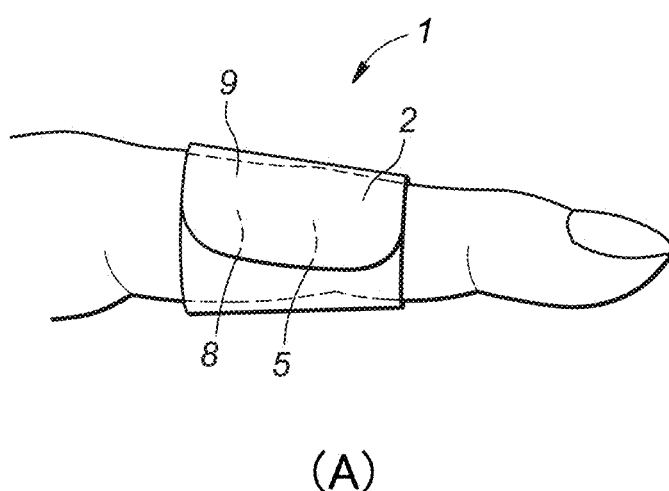
Figure 5:
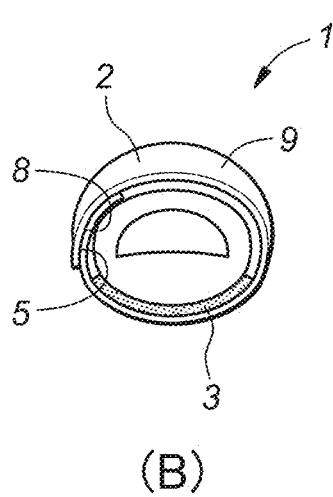
Figure 6:
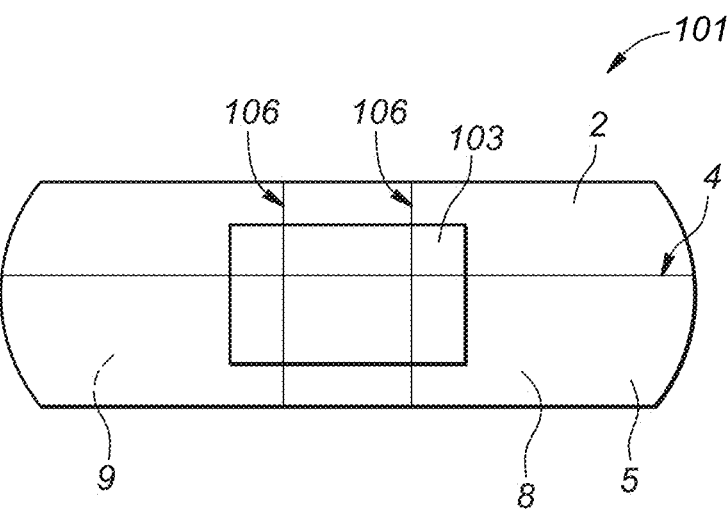
Figure 7:
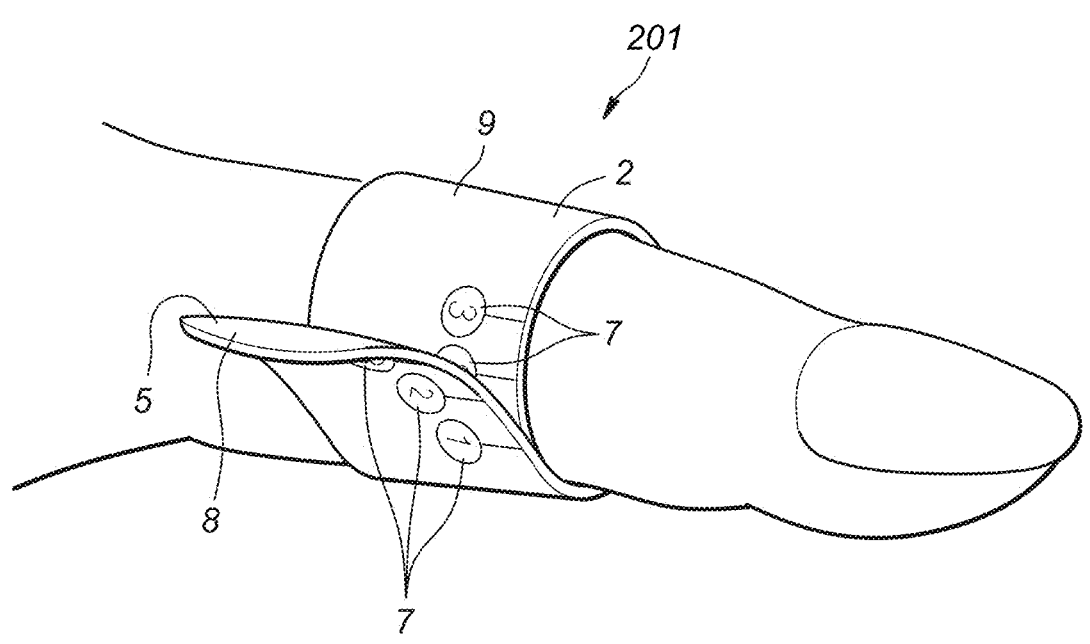

FIG. 4 a diagram illustrating the process of wrapping the finger brace of the first embodiment around a finger FIG. 5 a diagram illustrating a mode of use of the finger brace of the first embodiment FIG. 6 a view showing the finger brace according to a second embodiment of the present invention FIG. 7 a view showing the finger brace according to a third embodiment of the present invention

DESCRIPTION OF THE PREFERRED
EMBODIMENT(S)

A finger brace 1 according to an embodiment of the present invention will be described in the following with reference to the appended drawings.

First Embodiment

FIG. 1 shows a finger brace 1 according to the first embodiment of the present invention. The finger brace 1 includes a tape component 2 formed in a band shape. The tape component 2 is wrapped around the affected finger. The surface facing the finger when wrapped will be called the inner surface 8, and the opposite surface will be called the outer surface 9. The tape component 2 is formed by processing a foldable flexible material, such as urethane nonwoven fabric, polyvinyl chloride, stretchable cotton fabric, sponge sheet, urethane film, or olefin film, into a thin film, and thin metal material may also be added. The edges of the tape component 2 at the longitudinal ends are preferably each formed into an arcuate shape.

As shown in FIGS. 1 and 2, the pad 3 is provided on the inner surface 8 of the tape component 2 at a prescribed position along the longitudinal axis. The pad 3 is rectangular in shape, and has a longitudinal dimension covering approximately half the circumference of the finger on the palmar side thereof and a lateral dimension equal to or slightly smaller than the lateral dimension of the tape component 2. The longitudinal axis of the pad 3 refers to a direction parallel to the longitudinal axis of the tape component 2, and the lateral axis of the pad 3 refers to a direction parallel to the lateral axis of the tape component 2.

The pad 3 is made of a material that is elastically stretchable and is soft. The pad 3 is made of warp knitted or weft knitted fabric (knit) using yarns that have a straight or spiral structure and are made of cotton, rayon, polyester, etc., and may contain at least two layers of fabric. The pad 3 is preferably formed to have a texture that is less stretchable along the lateral axis than along the longitudinal axis. The level of stretchability can be determined by measuring the elongation using a constant-speed elongation tensile tester, and determining the stretchability according to the measured elongation. Since the pad 3 has a tissue that is less stretchable along the lateral axis than along the longitudinal axis, when the finger brace 1 is worn on the finger, bending of the affected area can be moderately suppressed while ensuring patient comfort. For example, the maximum bending angle of the finger on the palmar side when the finger brace 1 is worn may be within the range of about 20 degrees to 60 degrees.

The tape component 2 is provided with the adhesive part 5 to prevent the finger brace 1 from being dislodged from the finger during use. The adhesive part 5 may consist of an adhesive or the like provided on at least one of the inner surface 8 and the outer surface 9 of the tape component 2 along the longitudinal axis. The adhesive part 5 may be provided only on an end part of the inner surface 8 or the outer surface 9 of the tape component 2, or may be provided on the entire surface of the inner surface 8 of the tape component 2. In the latter case, the adhesive strength of the adhesive part 5 at the end of the longitudinal axis of the tape component 2 may be weaker than the adhesive strength of the adhesive part 5 in other parts. The adhesive part 5 is not limited to a layer of adhesive, but may also be provided in the form of a snap button, hook-and-loop fastener, or the like that can be suitably bonded or attached together depending on ease of manufacture. In FIG. 1, the adhesive part 5 consists of an adhesive layer applied to the entire inner surface 8 of the tape component 2. When the adhesive part 5 consists of an adhesive layer, the tape component 2 may be provided with a peelable paper or film (not shown in the drawings) that covers the adhesive part 5. By providing a peelable paper or film on the adhesive part 5, the adhesive part 5 is prevented from sticking to an unintended object when the finger brace 1 is not in use.

The midpoint of the pad 3 in the longitudinal axis does not coincide with the midpoint of the tape component 2 in the longitudinal axis, but is offset therefrom. In FIG. 1, the midpoint of the pad 3 in the longitudinal axis is offset by 0.5 cm from the midpoint of the tape component 2 in the longitudinal axis.

The finger brace 1 has a first guideline 4 that extends along the longitudinal axis of the tape component 2 on the inner surface 8 of the tape component 2. The first guideline 4 is provided at a position laterally offset from the midpoint of the tape component 2 along the lateral axis. The first guideline 4 extends from one end of the tape component 2 along the longitudinal axis, and through the pad 3, to the other end of the tape component 2 in the longitudinal axis. In FIG. 1, the first guideline 4 is configured as a line extending in the longitudinal axis and passing through a point dividing the tape component 2 in a 3-to-2 ratio along the lateral axis.

The finger brace 1 has a second guideline 6 provided on the inner surface 8 of the tape component 2 along the lateral axis of the tape component 2. The second guideline 6 is provided near one of the longitudinal ends of the pad 3. In particular, the second guideline 6 intersects the first guideline 4 at a right angle on the inner surface 8 of the pad 3.

A marking 10 is provided on the inner surface 8 of the tape component 2 at a longitudinal end-part thereof on a side toward which the midpoint of the pad 3 is offset along the longitudinal axis. The marking 10 may be a dot, line, number, or letter, or may be a region of the end of the tape component 2 colored in a specific color or with a geometric pattern. In the first embodiment, the marking 10 is formed by coloring the end part of the tape component 2 in red.

The dimension of the tape component 2 along the longitudinal axis may be, for example, about 4.0 to 8.0 cm. The dimension of the tape component 2 along the lateral axis may be, for example, about 2.0 to 4.0 cm. In the finger brace 1 of this embodiment, the dimension of the tape component 2 is 8 cm in the longitudinal axis, and the dimension along the lateral axis is 3.5 cm. The dimensions in the longitudinal axis and the lateral axis of the tape component 2 can be appropriately changed according to the thickness and length of the finger of the specific patient.

The dimension of the pad 3 along the longitudinal axis is selected to be the same as or larger than the dimension thereof along the lateral axis. The dimension of the pad 3 in the longitudinal axis may be, for example, about 1.5 to 4 cm. The dimension of the pad 3 in the axis may be, for example, about 1.5 cm to 3.5 cm. In the finger brace 1 of this embodiment, the dimension of the pad 3 along the longitudinal axis is 3 cm, and the dimension of the pad 3 in the lateral axis is 2 cm. The dimensions of the pad 3 along the longitudinal axis and the lateral axis can be changed as appropriate according to the thickness and length of the finger of the specific patient.

Next, a mode of using the finger brace 1 will be discussed in the following with reference to FIGS. 4 and 5. Here, the directions are determined as shown in the drawings, and in this example, the index finger of the left hand is affected by tendovaginitis. First, the patient takes the finger brace 1 in the hand and peels off the peelable paper or film (not shown in the drawings) covering the adhesive part 5. Next, as shown in FIG. 4, the patient fully extends the finger, and places the tape component 2 so that the marking 10 is positioned at the upper end, the inner surface 8 of the tape component 2 faces a side of the finger side, and the affected part (finger) is located between the finger brace 1 and the patient. At this point, the finger brace 1 should be positioned so that the finger brace 1 extends perpendicularly to the longitudinal axis of the finger and the first guideline 4 is offset toward the fingertip. Next, the patient positions the finger brace 1 such that the first guideline 4 coincides with the joint crease of the finger on the palmar side (proximal interphalangeal skin crease). Next, the patient adjusts the position of the finger brace 1 so that the palmar-side contour of the finger on which the finger brace 1 is to be worn is aligned with the second guideline 6. Next, the patient holds the end of the tape component 2 with the right hand and wraps the tape component 2 around the finger on which the finger brace 1 is to be worn under appropriate tension. FIG. 5(A) shows the state of the finger brace 1 when worn as discussed above, and FIG. 5(B) provides a view of the same state shown in FIG. 5(A) when viewed from the fingertip.

According to the finger brace 1 of this embodiment, the first guideline 4 is selected to be a line extending in the longitudinal axis that passes through the point that divides the tape component 2 in a 3-to-2 ratio along the lateral axis. As a result, by aligning the first guideline 4 with the joint crease of the finger on the palmar side, the patient can easily wrap the tape component 2 at a position that is appropriately aligned with the finger joint which is difficult to discern from outside. More specifically, as shown in FIG. 4, the center line 11 indicated by an imaginary line extending on the pad 3 along the longitudinal axis can be aligned with the PIP-J part located at the junction of the middle phalanx 12 and the proximal phalanx 13 of the finger. In addition, by providing the marking 10 at one end of the tape component 2 in the longitudinal axis, the patient can easily recognize the axis in which the finger brace 1 is to be placed for use.

In addition, by giving the pad 3 appropriate elasticity, the risk of excessively fixating the affected finger is removed. In addition, since the pad 3 is made of a material that easily stretches and contracts, the patient wearing the finger brace 1 can softly fix the affected part and appropriately suppress flexion and extension of the finger while ensuring comfort.

In addition, since the pad 3 is provided at a position offset from the midpoint of the tape component 2 with respect to the longitudinal axis, the pad 3 can be easily wrapped around the finger while aligning it with the exactly correct position on the palmar side of the finger.

In addition, the second guideline 6 is provided near one end of the pad 3 in the longitudinal axis. As a result, by aligning the second guideline 6 with the profile of the palmar side of the finger when viewed from a side, the patient can accurately and easily align the pad 3 with a position corresponding to the joint of the finger on the palmar side thereof while ensuring visual recognition of most of the pad 3 when wearing the finger brace 1.

In addition, since the adhesive strength of the adhesive part 5 at the end of the tape component 2 in the longitudinal axis is weaker than the adhesive strength of other parts of the adhesive part 5, the patient can easily remove the finger brace 1 by grasping the end of the tape component 2 with weak adhesive strength, even after securing the finger brace 1 in the wrong position, and the position of the finger brace 1 can therefore be readjusted.

In the above description of the mode of using the finger brace 1, the finger brace 1 was applied to the second joint (PIP-J) of the index finger of the left hand, but the finger brace 1 can also be applied to fingers other than the index finger such as the first joint (PIP-J: interphalangeal joint) of the thumb. The finger brace 1 can also be applied to fingers of the right hand in a similar manner.

Second Embodiment

The finger brace 101 according to a second embodiment of the present invention differs from that of the first embodiment in the positioning of the pad 3 and in the fact that two second guidelines 6 are provided. In the following description, only the parts that differ from those of the first embodiment are described, and the parts that are similar to those of the first embodiment are denoted with like numerals and omitted from the following description.

As shown in FIG. 6, the pad 103 is provided on the tape component 2 formed in a strip shape, similar to the finger brace 1 of the first embodiment. The midpoint of the pad 103 in the longitudinal axis coincides with the midpoint of the tape component 2 in the longitudinal axis. The finger brace 101 has two second guidelines 106 extending along the lateral axis of the tape component 2. The second guidelines 106 are positioned adjacent to the respective longitudinal ends of the pad 103. In particular, the second guidelines 106 both intersect with the first guideline 4 on the inner surface 8 of the pad 103.

By matching the midpoint of the pad 103 in the longitudinal axis to the midpoint of the tape component 2 in the longitudinal axis, and providing two second guidelines 106, the finger brace 101 can be worn on the fingers not only of the left hand but also of the right hand. The reason for this is given in the following. When wearing the finger brace 1 of the first embodiment, the first guideline 4 needs to be aligned with the position of the finger offset toward the fingertip side in FIG. 4. Therefore, when wrapping the finger brace 1 of the first embodiment around the finger of the right hand with the fingertip pointed to the left, the finger brace 1 needs to be placed between the affected part (finger) and the patient with the inner surface 8 of the tape component 2 facing toward the finger. As a result, seeing the first guideline 4 and the second guidelines 6 is difficult for the patient. Alternatively, the fingertip may be pointed to the right with the affected part (finger) positioned between the finger brace 1 and the patient. In this case, however, due to the limited range of motion of the wrist, wearing the finger brace 1 at an appropriate position of the finger is difficult for the patient. On the other hand, in the case of the finger brace 101 of the second embodiment, the finger brace 101 can be rotated 180 degrees or upside down so that the affected area (finger) is located between the finger brace 101 and the patient with the fingertip of the right hand pointed to the left. As a result, the first guideline 4, and the second guideline 106 can be seen by the patient, so the finger brace 101 can be easily worn.

Third Embodiment

The finger brace 201 according to a third embodiment of the present invention differs from the finger brace 1 of the first embodiment and the finger brace 101 of the second embodiment in that markings 7 are provided on the outer surface 9 of the tape component 2. These markings 7 indicate the wrapping thickness of the tape component 2 at the part where the two layers of the tape component 2 overlap with each other when the tape component 2 is wrapped around the finger. In the following description, only the parts that differ from those of the first embodiment will be described, and the parts similar to those of the first embodiment are denoted with reference numerals without repeating the description of such parts.

At least one marking 7 is provided on the outer surface 9 of each longitudinal end part of the tape component 2. The markings 7 may consist of, for example, dots, lines, digits, or letters. As shown in FIG. 7, in this embodiment, the markings 7 on each longitudinal end part of the tape component 2 include three digits of numerals one to three (1 to 3) arranged on the lateral edge of the tape component 2 at intervals. The patient can therefore adjust the wrapping tightness of the tape component 2 depending on the thickness of the finger and the level of healing by aligning one of the markings (such as "2") in one of the longitudinal end parts of the tape component 2 with the corresponding marking (such as "2") on the other longitudinal end part of the tape component 2.

This concludes the description of the specific embodiments of the present invention, but the present invention is not limited to the above embodiments and can be applied in a wide range of different modes. For example, one of the edges of the tape component 2 extending along the longitudinal axis may be longer than the other edge, so that when the tape component 2 is wrapped around a finger, the tape component 2 may open or flare toward the fingertip. In particular, the tape component 2 is preferably configured such that only the tape component 2 on the palmar side of the finger opens or flares toward the fingertip side when the finger brace 1, 101, 201 is worn. The patient can thus more easily bend the affected finger even when wearing the finger brace 1, 101, 201.

The tape component 2 may also have holes penetrating therethrough from the inner surface 8 to the outer surface 9 at least in a part thereof. This improves the breathability of the affected area when the finger brace 1, 101, 201 is worn and prevents lack of ventilation.

The thickness of the threads forming the pad 3, 103 may vary, and the pad 3, 103 may be formed by regularly varying the thicknesses of the weaving threads. For example, by using stiffer and thicker threads in the warp threads extending along the lateral axis than in the weft threads extending along the longitudinal axis, the pad 3, 103 can be configured to be less likely to stretch in the lateral axis than in the longitudinal axis. As a result, even when the patient is wearing the finger brace 1, 101, 201, the patient can moderately suppress but not hinder the bending and stretching of the affected part, resulting in less functional impairment in daily life. In addition, the threads constituting the pad 3, 103 may have a stretchable spiral structure. As a result, the patient can more easily bend and stretch the affected part even when wearing the finger brace 1, 101, 201 because of the increased ease of the stretching of the finger brace 1, 101, 201.

Further, the one longitudinal end part of the tape component 2 on which the markings 7 are provided may be smaller in lateral dimension than the other longitudinal end part of the tape component 2. When the patient wears the finger brace 201, the patient may wrap the tape component 2 so that the end part of the tape component 2 with a shorter length along the lateral axis overlaps the other end part. This makes visual recognition of the markings 7 provided at both longitudinal ends of the tape component 2 easier for the patient when wrapping the tape component 2 around the finger, and facilitates alignment of the markings 7 at both end parts of the tape component 2.

The finger braces 1, 101, 201 described above may be configured to be reusable or disposable. If the finger braces 1, 101, 201 is disposable, the patient can keep the affected area where the finger braces 1, 101, 201 is worn in a clean state.

When increased flexibility is desired in the finger braces 1, 101, 201 configured as described above, micro springs may be incorporated in the pad 3.

The finger braces 1, 101, 201 may also be provided to the patient in the form of a kit including instructions on how to use the finger braces 1, 101, 201.

| LIST OF REFERENCE NUMERALS | |
| --- | --- |
| 1: finger brace | 2: tape component |
| 3: pad | 4: first guideline |
| 5: adhesive part | 6: second guideline |
| 7: mark | 8: inner surface |
| 9: outer surface | |

The invention claimed is:

1. A finger brace, comprising:

a tape component formed in a band shape having prescribed length and width;

an elastically deformable pad provided at a prescribed position along a longitudinal axis of the tape component;

a first guideline provided on a surface of the tape component facing a finger when worn on the finger along the longitudinal axis of the tape component offset from a lateral midpoint of the tape component by a prescribed distance;

a second guideline extending along a lateral axis of the tape component provided on the pad adjacent to a longitudinal edge of the pad; and

an adhesive part provided on the tape component to join two layers of the tape component to each other when the tape component is wrapped around the finger, wherein the pad has a lateral dimension smaller than a lateral dimension of the tape component, and wherein the second guideline intersects the first guideline at a right angle on an inner surface of the pad, wherein the first guideline is configured to coincide with a joint crease of the finger on the palmar side; and wherein the second guideline is configured so that a palmar side contour of the finger on which the finger brace is to be worn is aligned with the second guideline.

2. The finger brace according to claim 1, wherein the first guideline is a line extending in the longitudinal axis of the tape component and passing through a point at which the tape component is divided by a ratio of 3 to 2 along the lateral axis of the tape component.

3. The finger brace according to claim 1, wherein the pad is 1.5 to 3.5 cm long along a longitudinal axis of the pad.

4. The finger brace according to claim 1, wherein the pad is made of a material that is structured to be less readily stretchable along a lateral axis of the pad than along a longitudinal axis of the pad.

5. The finger brace according to claim 4, wherein a midpoint of the pad along the longitudinal axis of the pad is offset to one side along the longitudinal axis of the tape component with respect to a midpoint of the tape component along the longitudinal axis of the tape component.

6. The finger brace according to claim 5, wherein marks indicating a wrapping thickness of the tape component are provided at parts of the tape component where the tape component overlaps with itself when wrapped around the finger.

* * * * *